United States Patent [19]

Imaizumi et al.

[11] Patent Number: 4,656,287
[45] Date of Patent: Apr. 7, 1987

[54] AMINOTHIAZOLE INTERMEDIATE FOR A CEPHALOSPORIN

[75] Inventors: Hiroyuki Imaizumi, Toyama; Takihiro Inaba, Namerikawa; Seishi Morita; Ryuko Takeno, both of Toyama; Yoshiharu Murotani; Hirohiko Fukuda, both of Toyama; Junichi Yoshida; Kiyoshi Tanaka, both of Toyama; Shuntaro Takano; Isamu Saikawa, both of Toyama, all of Japan

[73] Assignee: Toyoma Chemical Co., Ltd., Tokyo, Japan

[21] Appl. No.: 753,942

[22] Filed: Jul. 11, 1985

Related U.S. Application Data

[62] Division of Ser. No. 655,457, Sep. 28, 1984.

[30] Foreign Application Priority Data

May 25, 1984 [JP] Japan ................................. 59-104759
Sep. 17, 1984 [JP] Japan ................................. 59-192635

[51] Int. Cl.$^4$ ........................................... C07D 277/38
[52] U.S. Cl. ..................................... 548/194; 540/222
[58] Field of Search ........................................ 548/194

[56] References Cited

U.S. PATENT DOCUMENTS 4,283,396  8/1981  Heymes ............................. 540/228

FOREIGN PATENT DOCUMENTS

A0023453  2/1981  European Pat. Off. .
OS3137854  4/1982  Fed. Rep. of Germany .
OS3341591  5/1984  Fed. Rep. of Germany .
A2348219  11/1977  France .
A2461712  2/1981  France .
100772  8/1981  Japan ................................. 548/194

OTHER PUBLICATIONS

March, Advanced Organic Chemistry 2nd Ed., p. 388 (1980).
Ochiai, J. of Antibiotics 34(2), pp. 160–170 (1981).
Houben–Weyl, Methoden der Organischen Chemie, vol. XI/2, 1958, pp. 23–25.
Chemical Abstracts, vol. 82, 1975, 156338v.
Gattermann–Wieland, Die Praxis des Organischen Chemikers, 43rd Ed., 1982, pp. 313–314.

Primary Examiner—Robert J. Warden
Assistant Examiner—Robert Benson
Attorney, Agent, or Firm—Oblon, Fisher, Spivak, McClelland & Maier

[57] ABSTRACT

This invention relates to a novel aminothiazole intermediate for production of a cephalosporin of antibiotic activity.

1 Claim, No Drawings

AMINOTHIAZOLE INTERMEDIATE FOR A CEPHALOSPORIN

This application is a division of copending application Ser. No. 655,457, filed on Sept. 28, 1984.

This invention relates to a novel process for producing a cephalosporin, an intermediate for the cephalosporin, and a process for producing the intermediate.

The present inventors previously found that a cephalosporin (syn-isomer) represented by the formula [I] or a salt thereof.

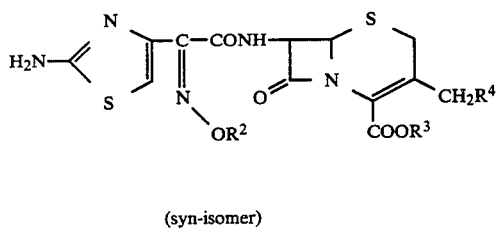

(syn-isomer)

wherein $R^2$ is a lower alkyl group; $R^3$ is a hydrogen atom or a carboxyl-protecting group; and $R^4$ is a substituted or unsubstituted heterocyclic group attached to the exomethylene group at the 3-position of the cephem ring through a carbon-nitrogen bond, are very useful as an anti-bacterial agent and applied for a patent thereon (Japanese Patent Application Kokai (Laid-Open) Nos. 99,592/82 and 93,085/84 and Japanese Patent Application Nos. 67,871/83, 113,565/83 and 114,313/83).

Since then, the present inventors have conducted extensive research on processes for producing the cephalosporin represented by the formula [I] or a salt thereof. As a result, they have found that the useful cephalosporin (syn-isomer) represented by the formula [I] or a salt thereof can be readily obtained in a high yield by reacting a compound (syn-isomer) represented by the formula [II]:

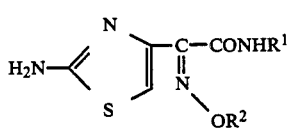

(syn-isomer)

wherein $R^1$ is a hydrogen atom or a substituted or unsubstituted alkyl, aralkyl, aryl or heterocyclic group; and $R^2$ is a lower alkyl group, with a compound represented by the formula [III]:

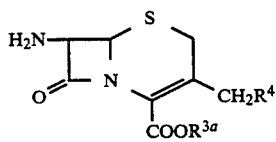

wherein $R^{3a}$ is a carboxyl-protecting group; and $R^4$ is a substituted or unsubstituted heterocyclic group attached to the exomethylene group at the 3-position of the cephem ring through a carbon-nitrogen bond, in the presence of boron trifluoride or a complex compound thereof, and then, if desired, removing the carboxyl-protecting group or converting the product to a salt.

An object of this invention is to provide a novel process for readily producing a useful cephalosporin (syn-isomer) represented by the formula [I] or a salt thereof.

Another object of this invention is to provide a novel process for readily producing a useful cephalosporin (syn-isomer) represented by the formula [I] or a salt thereof with a high purity in a high yield.

A further object of this invention is to provide a novel intermediate (syn-isomer) represented by the formula [II] for use in the above-mentioned production process.

A still further object of this invention is to provide a process for producing the intermediate.

Other objects and advantages of this invention will be apparent from the following description.

This invention will be explained in detail below.

According to this invention, there is provided a process for producing a cephalosporin represented by the formula [I] or a salt thereof:

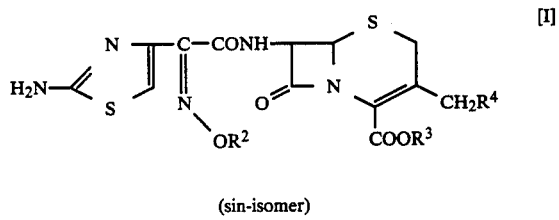

(sin-isomer)

wherein $R^2$, $R^3$ and $R^4$ have the same meanings as defined above, which comprises reacting a compound represented by the formula [II]:

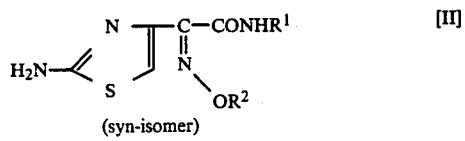

(syn-isomer)

wherein $R^1$ and $R^2$ have the same meanings as defined above, with a compound represented by the formula [III]:

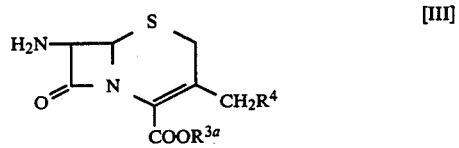

where $R^{3a}$ and $R^4$ have the same meanings as defined above, in the presence of boron trifluoride or a complex compound thereof, and then, if desired, removing the carboxyl-protecting group or converting the product to a salt thereof.

That is to say, a cephalosporin represented by the formula [I] or a salt thereof is readily obtained in a high yield by reacting an acid amide or a mono-substituted acid amide represented by the formula [II], which has a free amino group at the 2-position of the thiazole ring, with a compound represented by the formula [III] in the presence of boron trifluoride or a complex compound thereof.

This invention also provides a novel intermediate represented by the formula [II] for producing a useful cephalosporin:

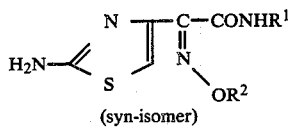

(syn-isomer)

wherein $R^1$ and $R^2$ have the same meanings as defined above, and further provides a process for producing the intermediate represented by the formula [II], which comprises reacting a compound represented by the formula [IV]:

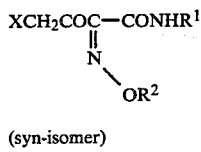

(syn-isomer)

wherein X is a halogen atom and $R^1$ and $R^2$ have the same meanings as defined above, with thiourea.

This invention will be further explained in detail below.

Unless otherwise specified, in this specification, the term "alkyl" means a straight or branched chain $C_{1-14}$ alkyl group, for example, methyl, ethyl, n-propyl, isopropyl, n-butyl, isobutyl, sec-butyl, tert-butyl, pentyl, hexyl, heptyl, octyl, dodecyl or the like; the term "alkenyl" means a $C_{2-10}$ alkenyl group, for example, vinyl, allyl, isopropenyl, butenyl, 2-pentenyl or the like; the term "aryl" means, for example, phenyl, tolyl, naphthyl, indanyl or the like; the term "aralkyl" means, for example, benzyl, phenethyl, 4-methylbenzyl, naphthylmethyl or the like; the term "acyl" means a $C_{1-12}$ acyl group, for example, formyl, acetyl, propionyl, n-butyryl, isobutyryl, valeryl, pivaloyl, pentanecarbonyl, cyclohexanecarbonyl, benzoyl, naphthoyl, furoyl, thenoyl or the like; and the term "halogen" means fluorine, chlorine, bromine, iodine or the like. Also, the term "lower" means 1 to 5 carbon atoms.

Moreover, when there are words such as "alkyl", "alkenyl", "aryl", "aralkyl", "acyl", "lower" and the like in various terms used in this specification, they have the same meanings as mentioned above unless otherwise specified.

In the formula [II], $R^1$ is a hydrogen atom or a substituted or unsubstituted alkyl, aralkyl, aryl or heterocyclic group. The heterocyclic group includes specifically nitrogen-containing 5- or 6-membered heterocyclic groups such as pyrazoyl, imidazolyl, triazolyl, tetrazolyl, pyridyl, pyrimidinyl, pyridazinyl, pyrazinyl, triazinyl and the like. The substituent on $R^1$ includes, for example, a halogen atom, a nitro group, an alkyl group, an aryl group, an alkoxy group, an alkylthio group, a cyano group, an amino group, an alkylamino group, a dialkylamino group, an acylamino group, an acyl group, an acyloxy group, an acylalkyl group, a carboxyl group, an alkoxycarbonyl group, an alkoxycarbonylalkyl group, a carbamoyl group, an aminoalkyl group, an N-alkylaminoalkyl group, an N,N-dialkylaminoalkyl group, a hydroxyalkyl group, a hydroxyiminoalkyl group, an alkoxyalkyl group, a carboxyalkyl group, a sulfoalkyl group, a sulfo group, a sulfamoylalkyl group, a sulfamoyl group, a carbamoylalkyl group, a carbamoylalkenyl group, an N-hydroxycarbamoylalkyl group and the like. The above-mentioned alkyl, aralkyl, aryl or heterocyclic group for $R^1$ may be substituted by one or more of these substituents. Among these substituents, the carboxyl group may be protected with a carboxyl-protecting group which will be explained hereinafter as to $R^{3a}$ and $R^3$.

$R^{3a}$ is a carboxyl-protecting group, and $R^3$ is a hydrogen atom or a carboxyl-protecting group. The carboxyl-protecting group includes groups which are conventionally used as a carboxyl-protecting group in the fields of penicillin and cephalosporin. They specifically include, for example, alkyl; phthalidyl; diphenylmethyl; $C_{2-7}$acyloxy-$C_{1-5}$alkyl such as acetoxymethyl, pivaloyloxymethyl, propionyloxymethyl, butyryloxymethyl, isobutyryloxymethyl, valeryloxymethyl, 1-acetoxyethyl, 1-acetoxy-n-propyl, 1-pivaloyloxyethyl, 1-pivaloyloxy-n-propyl, benzoyloxymethyl, 1-benzoyloxyethyl and the like; α-$C_{2-5}$acyloxybenzyl such as α-pivaloyloxybenzyl, α-acetoxybenzyl and the like; etc.

Furthermore, $R^4$ is a substituted or unsubstituted heterocyclic group attached to the exomethylene group at the 3-position of the cephem ring through a carbon-nitrogen bond, and the heterocyclic group includes, for example, tetrazolyl, triazolyl, (di- or tetra-hydro)pyrazinyl, (di- or tetra-hydro)pyridazinyl, dihydropyrimidinyl, and five- or six-membered cyclic groups represented by the formula,

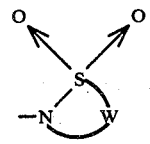

in which W is a divalent group, for example, 1,2,6-thiadiazin-1,1-dioxide-2-yl, isothiazolidin-1,1-dioxide-2-yl and the like. More specifically, said heterocyclic group includes 1-(1,2,3,4-tetrazolyl), 2-(1,2,3,4-tetrazolyl), 1-(1,2,3-triazolyl), 2-(1,2,3-triazolyl), 1-(1,2,4-triazolyl), 4-(1,2,4-triazolyl), 2,3-dioxo-1,2,3,4-tetrahydropyrazinyl, 3,6-dioxo-1,2,3,6-tetrahydropyridazinyl, 6-oxo-1,6-dihydropyridazinyl, 2-oxo-1,2-dihydropyrazinyl, 6-oxo-1,6-dihydropyrimidinyl, 2-oxo-1,2-dihydropyrimidinyl, 1,2,6-thiadiazin-1,1-dioxide-2-yl, isothiazolidin-1,1-dioxide-2-yl and the like.

As the substituents on the heterocyclic group for $R^4$, there may be used those substituents which have been described as to $R^1$. Among these substituents, the carboxyl group may be protected with the carboxyl-protecting group described as to $R^{3a}$ and $R^3$.

The salts of the cephalosporin represented by the formula [I] include salts at the basic groups and the acidic groups which have conventionally been well-known in the fields of penicillin and cephalosporin. The salts at the basic groups include, for example, salts with mineral acids such as hydrochloric acid, hydrobormic acid, hydriodic acid, nitric acid, sulfuric acid and the like; salts with organic carboxylic acids such as oxalic acid, succinic acid, formic acid, trichloroacetic acid, trifluoroacetic acid and the like; and salts with sulfonic acids such as methanesulfonic acid, ethanesulfonic acid, benzenesulfonic acid, toluene-2-sulfonic acid, toluene-4-sulfonic acid, mesitylenesulfonic acid (2,4,6-trimethylbenzenesulfonic acid) and the like. The salts at the acidic groups include, for example, salts with alkali metals such as sodium, potassium and the like; salts with alkaline earth metals such as calcium, magnesium and the like; ammonium salts; and salts with nitrogen-containing organic bases such as triethylemine, trimethylamine, aniline, N,N-dimethylaniline, pyridine, dicyclohexylamine and the like.

The embodiments of the processes of this invention will be described below.

(a) Process for producing a cephalosporin of the formula [I] or a salt thereof (i) The cephalosporin represented by the formula [I] or a slat thereof can be obtained by reacting a compound represented by the formula [II] with a compound represented by the formula [III] in the presence of boron trifluoride or a complex compound thereof, and then, if desired, removing the carboxyl-protecting group or converting the product to a salt.

The compound represented by the formula [III] is readily obtained by subjecting 7-aminocephalosporanic acid to a 3-position-conversion in the process of an acid (Japanese Patent Application Kokai (Laid-Open) Nos. 99,592/82, 93,085/84 and 98,089/84 and Japanese Patent Application Nos. 67,871/83, 113,565/83 and 114,313/83 and the like) and then introducing a protecting group into a carboxyl group at the 4-position.

The complex compound of boron trifluoride which is used in this invention includes, for example, complex compounds of boron trifluoride with a carboxylic acid ester such as ethyl formate, ethyl acetate or the like; with a dialkyl ether such as diethyl ether, diisopropyl ether or the like; with sulfolane; and with a nitrile such as acetonitrile, propionitrile or the like, and preferred are a sulfolane complex compound, an acetonitrile complex compound, a diethyl ether complex compound and an ethyl acetate complex compound of boron trifluoride.

Also, in this invention, it is preferable to carry out the reactions in an organic solvent, and the organic solvent to be used includes, for example, nitroalkanes such as nitromethane, nitroethane, nitropropane and the like, ethers such as diethyl ether, diisopropyl ether, dioxane, tetrahydrofuran, ethylene glycol dimethyl ether, anisole and the like; esters such as ethyl formate, diethyl carbonate, methyl acetate, ethyl acetate, diethyl oxalate, ethyl chloroacetate, butyl acetate and the like; halogenated hydrocarbons such as methylene chloride, chloroform, 1,2-dichloroethane and the like; nitriles such as acetonitrile, propionitrile and the like; ketones such as acetone and the like; sulfolane; etc., and preferred are nitroalkanes, esters, nitriles, halogenated hydrocarbons and sulfolane. If desired, it is also possible to use a mixed solvent of two or more of these organic solvents. Furthermore, a complex compound formed with such an organic solvent and boron trifluoride may be used as a solvent.

The amount of the compound represented by the formula [II] to be used is usually 0.7–5 moles, preferably 1–3 moles, per mole of the compound represented by the formula [III]. And the amount of boron trifluoride or its complex compound to be used is usually 1–3 moles per mole of the compound represented by the formula [II].

The reaction is generally completed at −10° C. to 50° C. in a period of 10 minutes to 20 hours.

In this reaction, the sequence of adding the compounds represented by the formulas [II] and [III] and boron trifluoride (or a complex compound of boron trifluoride) is not critical. However, it is preferable to react first the compound represented by the formula [II] with boron trifluoride or a complex compound thereof and then react the reaction product with the compound represented by the formula [III].

Moreover, it is preferred that a compound which is obtained by reacting the compound represented by the formula [II] with boron trifluoride or a complex compound thereof be isolated and then the isolated compound be reacted with the compound represented by the formula [III]. In this case, the amount of boron trifluoride or its complex compound used is 2 moles or more, preferably 2–3 moles, per mole of the compound represented by the formula [II]. The compound obtained by the reaction of the compound represented by the formula [II] with boron trifluoride or a complex compound thereof is usually used in an amount of 1–2 moles (in terms of the compound represented by the formula [II]) per mole of the compound represented by the formula [III].

(ii) Moreover, even when the compound represented by the formula [III] obtained in the process of producing the compound represented by the formula [III] is used without isolation as the starting compound of the process of this invention, the use of the following method gives a favorable result as in the case of an isolated compound of the formula [III] being the starting compound:

A compound (syn-isomer) represented by the formula [II-a].

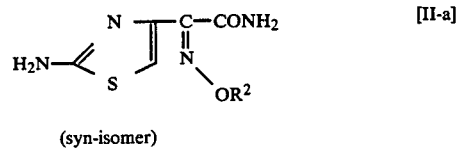

(syn-isomer)

wherein $R^2$ has the same meaning as defined above, is reacted with boron trifluoride or a complex compound thereof, the compound thus obtained is reacted with the compound represented by the formula [III] at −50° C. to 0° C. in the above-mentioned organic solvent to produce an intermediate (first reaction stage),

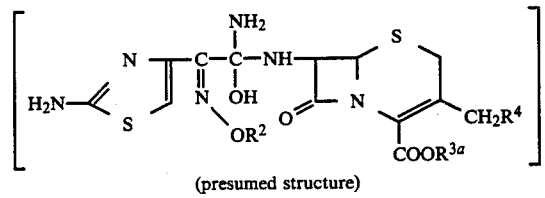

(presumed structure)

wherein $R^2$, $R^{3a}$ and $R^4$ have the same meanings as defined above, and then the reaction mixture is subjected to further reaction at 0° C. to 50° C. at a pH of 4.5 to 6.7 in a mixed solvent of water and the organic solvent (second reaction stage), whereby a cephalosporin represented by the formula [I] or a salt thereof is produced in high purity and high yield. Thus, even when the unisolated compound of the formula [III] is used as the starting compound, the above method (ii) can prevent the intermediate from being decomposed, and hence, can fulfill the purpose of this invention.

As a complex compound of boron trifluoride in this reaction, there may be used the same compounds as mentioned above. The amount of the compound of the formula [III] used, the amount of boron trifluoride or its complex compound to be used and the amount of the compound obtained by reacting the compound of the formula [II-a] with boron trifluoride or its complex compound are as mentioned above.

As the mixed solvent of water and an organic solvent, there may be used mixed solvents of water and the above-mentioned organic solvents, and particularly, mixed solvents which form a two-layer system are preferred.

When the reaction (the second reaction stage) is conducted in a mixed solvent of water and an organic solvent at a pH of 4.5–6.7 at 0° C. to 50° C., the pH value is appropriately controlled and maintained in the above pH range using a base and/or a buffer which are conventionally used. In this case, the reaction is preferably conducted at a pH of 6.2–6.5. When the reaction is conducted in a pH range of 4.5–6.0, it is preferable to adjust the pH in the presence of a salt. The base used in this reaction includes inorganic bases which are conventionally used for the adjustment of a pH value, for example, alkali metal carbonates such as sodium carbonate, potassium carbonate and the like; alkali metal hydrogencarbonates such as sodium hydrogencarbonate, potassium hydrogen-carbonate and the like; alkali metal hydroxides such as sodium hydroxide, potassium hydroxide and the like; alkali metal phosphates such as socium dihydrogenphosphate, disodium hydrogenphosphate, trisodium phosphate, potassium dihydrogenphosphate, dipotassium hydrogenphosphate, tripotassium phosphate; and alkali metal acetates such as sodium acetate, potassium acetate and the like. The buffer includes buffer solutions which are conventionally used for pH-adjustment such as buffer solutions using phosphoric acid, boric acid, acetic acid, tri(hydroxymethyl)aminomethane or the like. And the salt used in the reaction includes inorganic salts such as sodium chloride and the like.

The first reaction stage in which the reaction is conducted at −50° C. to 0° C. in an organic solvent is usually completed in a period of 10 minutes to 10 hours. In this case, the reaction is completed in a shorter time as the reaction temperature becomes higher, and the reaction is usually completed within about 1 hour at −5° C. to 0° C. And the second reaction stage in which the reaction is effected at 0° C. to 50° C. is usually completed in a period of 10 minutes to 20 hours.

The cephalosporin of the formula [I] or a salt thereof thus obtained can be isolated and purified by a conventional method, and then, if desired, the compound of the formula [I] wherein $R^3$ is a carboxyl-protecting group can be readily converged in a conventional manner to a corresponding compound wherein $R^3$ is a hydrogen atom or a salt thereof.

Further, this invention covers all the optical isomers, racemic compounds, and all crystal forms and hydrates of the compounds represented by the formula [I] or a salt thereof.

(b) Process for producing the compound of the formula [II]

The compound of the formula [II] can be produced, for example, according to the production process shown below.

The compound of the formula [II] of this invention is a novel compound and a useful intermediate for a useful cephalosporin, for example, the cephalosporin represented by the formula [I].

The present invention covers all of the solvates, adducts, crystal forms and hydrates of the compound of the formula [II].

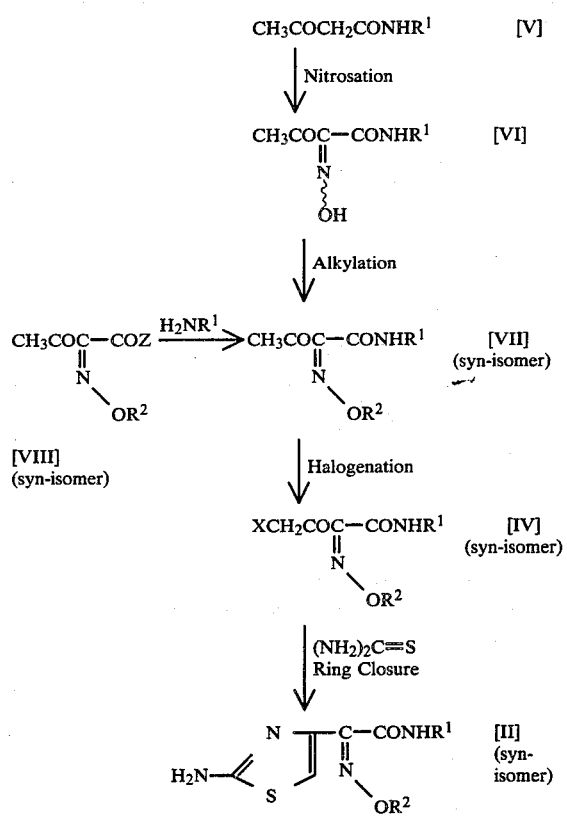

wherein $R^1$, $R^2$ and X have the same meanings as defined above; Z is a halogen atom or a group represented by the formula $-OR^1$ or $-SR^1$ (in which $R^1$ has the same meaning as defined above); and the bond∼means that the compound may be a syn- or anti-isomer or a mixture thereof.

(1) Production of the compound of the formula [VI]

A nitroso compound represented by the formula [VI] can be obtained by reacting a compound represented by the formula [V] with a nitrosating agent.

The reaction is usually conducted in a solvent, and the solvent used includes solvents inert to the reaction such as water, acetic acid, benzene, methanol, ethanol, tetrahydrofuran and the like. These solvents may be used in admixture of two or more.

The preferred nitrosating agents used in this reaction are nitrous acid and derivatives thereof, for example, nitrosyl halides such as nitrosyl chloride, nitrosyl bromide and the like; alkali metal nitrites such as sodium nitrite, potassium nitrite and the like; and alkyl nitrites such as butyl nitrite, pentyl nitrite and the like. When an alkali metal nitrite is used as the nitrosating agent, the reaction is preferably carried out in the presence of an inorganic or organic acid such as hydrochloric acid, sulfuric acid, formic acid, acetic acid or the like. When an alkyl nitrite is used as the nitrosating agent, it is preferable to effect the reaction in the presence of a strong base such as an alkali metal alkoxide.

This reaction is completed at 0° C. to 30° C. in a period of 10 minutes to 10 hours.

(2) Production of the compound of the formula [VII]

The compound represented by the formula [VII] can be obtained by reacting a compound represented by the formula [VI] with an alkylating agent.

This reaction can be conducted according to a conventional method and is usually completed at −20° C. to 60° C. in a period of 5 minutes to 10 hours.

Any solvent may be used as far as it does not affect the reaction adversely, and it includes, for example, ethers such as diethyl ether, tetrahydrofuran, dioxane and the like; alcohols such as methanol, ethanol and the like; halogenated hydrocarbons such as chloroform, methylene chloride and the like; esters such as ethyl acetate, butyl acetate and the like; amides such as N,N-dimethylformamide, N,N-dimethylacetamide and the like; water; etc. These solvents may also be used in admixture of two or more.

The alkylating agent used in the reaction includes, for example, lower alkyl halides such as methyl iodide, methyl bromide, ethyl iodide, ethyl bromide and the like; dimethyl sulfate; diethyl sulfate; diazomethane; diazoethane; methyl p-toluenesulfonate; and the like. When an alkylating agent other than diazomethane or diazoethane is used in the reaction, it is preferable to effect the reaction in the presence of an inorganic or organic base, for example, an alkali metal carbonate such as sodium carbonate, potassium carbonate or the like; an alkali metal hydroxide such as sodium hydroxide, potassium hydroxide or the like; triethylamine; pyridine; N,N-dimethylaniline; or the like.

The compound represented by the formula [VII] can also be obtained by subjecting the compound of the formula [VIII] to an amidation reaction known per se using ammonia or a primary amine.

(3) Production of the compound of the formula [IV]

The compound represented by the formula [IV] can be obtained by reacting a compound represented by the formula [VII] with a halogenating agent.

The reaction is usually conducted in a solvent, and the solvent used includes solvents which do not affect the reaction adversely, for example, halogenated hydrocarbons such as ethylene chloride, chloroform and the like; organic carboxylic acids such as acetic acid, propionic acid and the like; ethers such as diethyl ether, tetrahydrofuran, dioxane and the like; alcohols such as methanol, ethanol, isopropanol and the like; etc. These solvents may also be used in admixture of two or more.

The reaction is usually completed at 0° C. to 50° C. in a period of 30 minutes to 24 hours.

The halogenating agent to be used includes, for example, halogens such as bromine, chlorine and the like; sulfuryl halides such as sulfuryl chloride and the like; hypohalous acids or alkali metal hypohalites such as hypochlorous acid, hypobromous acid, sodium hypochlorite and the like; N-halogenated imide compounds such as N-bromosuccinimide, N-chlorosuccinimide, N-bromophthalimide and the like; perbromide compounds such as pyridinium hydrobromide-perbromide, 2-carboxyethyltriphenylphosphoniumperbromide and the like; etc.

(4) Production of the compound of the formula [II]

The compound represented by the formula [II] can be obtained by reacting a compound represented by the formula [IV] with thiourea.

The reaction is usually conducted in a solvent, and as this solvent, any solvent may be used as far as it does not affect the reaction adversely. This includes water; alcohols such as methanol, ethanol and the like; ketones such as acetone and the like; ethers such as diethyl ether, tetrahydrofuran, dioxane and the like; amides such as N,N-dimethylformamide, N,N-dimethylacetamide and the like; N-methyl-α-pyridone and the like. These solvents may also be used in admixture of two or more.

The reaction sometimes proceeds smoothly by adding an acid-binding agent. And the acid-binding agent to be used includes, for example, inorganic or organic bases such as alkali metal hydroxides, alkali metal hydrogencarbonates, triethylamine, pyridine, N,N-dimethylaniline and the like.

The reaction is usually completed at 0° C. to 100° C. in a period of 1 to 48 hours, preferably 1 to 10 hours.

The thiourea can be used in a proportion of one to several moles per mole of the compound of the formula [IV].

As described above, the syn-isomer (the formula [II]) can be selectively obtained in a high yield at a low cost.

This invention will be illustrated below referring to Examples. However, this invention is not limited thereto.

EXAMPLE 1

(1) In 35 ml of water was dissolved 10.1 g of acetoacetamide, and 6.9 g of sodium nitrite was added to the resulting solution with ice-cooling, after which 25 ml of 4N sulfuric acid was added dropwise to the resulting mixture with stirring at 0° C. to 5° C. over a period of 30 minutes. After completion of the dropwise addition, the mixture was subjected to reaction at the same temperature for 30 minutes, and the pH was then adjusted to 6.0 with saturated aqueous sodium hydrogencarbonate solution.

After the insolubles had been removed, water was removed by distillation under reduction pressure. To the residue thus obtained was added 20 ml of ethyl acetate, and crystals thus obtained were collected by filtration to obtain 8.6 g (yield, 66.2%) of 2-hydroxyimino-3-oxobutyramide having a melting point of 96°–97° C.

IR(KBr) cm$^{-1}$: $\nu_{C=O}$ 1670

NMR (d$_6$-DMSO) δ value: 2.26 (3H, s, CH$_3$CO—), 7.46 (1H, bs,

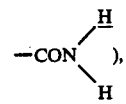

), 7.62 (1H, bs,

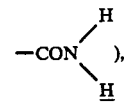

), 12.60 (1H, s, =N—OH)

(2) In 30 ml of water were dissolved 6.5 g of 2-hydroxyimino-3-oxobutyramide and 5.6 g of anhydrous sodium carbonate at 20° C. Furthermore, 6.6 g of dimethyl sulfate was added to the resulting solution at 20° C. to 25° C., and the resulting mixture was subjected to reaction at the same temperature for 2 hours. The precipitates thus formed were collected by filtration, and 100 ml of methanol was added to the precipitates, whereafter the resulting mixture was stirred at 40° C. to 50° C. for 30 minutes. After the insolubles had been removed, the solvent was removed by distillation under reduced pressure. To the residue thus obtained was added 20 ml of ethanol, and the crystals thus formed were collected by filtration to obtain 5.2 g (yield, 72.2%) of 2-(syn)-methoxyimino-3-oxobutyramide having a melting point of 156°–157° C.

IR(KBr) cm$^{-1}$: $\nu_{C=O}$ 1700, 1670

NMR (d$_6$-DMSO) δ value: 2.26 (3H, s, CH$_3$CO—), 3.96 (3H, s, —OCH$_3$), 7.46 (1H, bs,

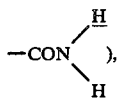
), 7.58 (1H, bs,

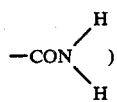
)

(3) In 36 ml of tetrahydrofuran was suspended 7.2 g of 2-(syn)-methoxyimino-3-oxobutyramide, and 0.8 g of bromine was added to the suspension with stirring at 40° C. After the disappearance of the color due to bromine was confirmed, 7.2 g of bromine was further added to the suspension with stirring at 25° C. to 30° C. After the suspension was subjected to reaction at the same temperature for 1 hour, the solvent was removed by distillation under reduced pressure. To the residue obtained were added 50 ml of ethyl acetate and 20 ml of water, and the pH was then adjusted to 6.0 with saturated aqueous sodium hydrogencarbonate solution. The organic layer was separated and washed with 20 ml of saturated aqueous sodium chloride solution. The organic layer was then dried over anhydrous magnesium sulfate, and the solvent was removed by distillation under reduced pressure. To the residue thus obtained was added 20 ml of a mixed solvent of diisopropyl ether-ethyl acetate (1:1), and the crystals thus formed were collected by filtration to obtain 9.2 g (yield, 82.1%) of 4-bromo-2-(syn)-methoxyimino-3-oxobutyramide having a melting point of 112°–113° C.

IR(KBr) cm$^{-1}$: $\nu_{C=O}$ 1715, 1660

NMR (d$_6$-DMSO) δ value: 4.02 (3H, s, —OCH$_3$), 4.58 (2H, s, BrCH$_2$CO—), 7.72 (2H, bs, —CONH$_2$)

(4) In 13.5 ml of ethanol was suspended 4.5 g of 4-bromo-2-(syn)-methoxyimino-3-oxobutyramide. To the suspension was added 1.5 g of thiourea, and the resulting mixture was subjected to reaction at 20° C. to 30° C. for 1 hour. The precipitated crystals were collected by filtration, washed with ethanol and thereafter suspended in 25 ml of water. The pH of the resulting suspension was adjusted to 6.0 with saturated aqueous sodium hydrogencarbonate solution. Then, the crystals thus formed were collected by filtration and recrystallized from 15 ml of a mixed solvent of water-methanol (1:1) to obtain 2.9 g (yield, 71.8%) of 2-(2-aminothiazol-4-yl)-2-(syn)-methoxyiminoacetamide having a melting point of 208°–209° C.

IR(KBr) cm$^{-1}$: $\nu_{C=O}$ 1665

NMR (d$_6$-DMSO) δ value: 3.84 (3H, s, —OCH$_3$), 6.75 (1H, s,

), 7.26 (2H, bs, —NH$_2$), 7.61 (1H, bs,

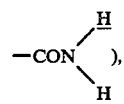
), 7.91 (1H, bs,

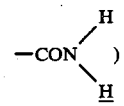
)

The compounds shown in Table 1 were obtained in a similar manner.

TABLE 1

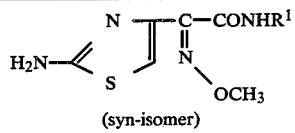

(syn-isomer)

| Compound R$^1$ | Melting point (°C.) | IR(KBr) cm$^{-1}$: $\nu_{C=O}$ | NMR (d$_6$-DMSO) δ value: |
|---|---|---|---|
| —CH$_2$CH$_3$ | 223–225 | 1640 | 1.08 (3H, t, J=7Hz, —CH$_2$CH$_3$), 3.18 (2H, m, —CH$_2$CH$_3$), 3.81 (3H, s, —OCH$_3$), 6.71 (1H, s, [thiazole]), 7.15 (2H, bs, —NH$_2$), 8.31 (1H, t, J=6Hz, —CONH—) |
| —C$_6$H$_5$ (phenyl) | 195–198 | 1655 | 3.95 (3H, s, —OCH$_3$), 6.93 (1H, s, [thiazole]), 7.11–7.50 (3H, m, [phenyl-H]), 7.31 (2H, bs, —NH$_2$), |

TABLE 1-continued $$H_2N-\underset{S}{\overset{N}{\bigvee}}\underset{}{\overset{}{\bigvee}}\underset{\underset{OCH_3}{N}}{\overset{C-CONHR^1}{\|}}$$

(syn-isomer)

| Compound R[1] | Melting point (°C.) | IR(KBr) cm$^{-1}$: $\nu_{C=O}$ | NMR (d$_6$-DMSO) δ value: |
|---|---|---|---|
| —⟨◯⟩—NO₂ | 249–250 | 1690 | 3.92 (3H, s, —OCH₃), 6.97 (1H, s, thiazole-H), 7.28 (2H, bs, —NH₂), 7.92, 8.27 (4H, ABq, J=9Hz, aromatic H), 11.28 (1H, s, —CONH—) |
| —⟨◯⟩N (4-pyridyl) | 239–242 | 1670 | 3.84 (3H, s, —OCH₃), 6.88 (1H, s, thiazole-H), 7.20 (2H, bs, —NH₂), 7.32–7.79 (2H, m, pyridyl-H), 8.12–8.65 (2H, m, pyridyl-H), 10.95 (1H, bs, —CONH—) |

Previous row (partial, from prior page): 7.65–7.88 (2H, m, aromatic H), 10.70 (1H, s, —CONH—)

EXAMPLE 2

(1) In 43 ml of methanol containing 3.6 g of hydrogen chloride was suspended 14.4 g of 2-(syn)-methoxyimino-3-oxobutyramide, and 16.0 g of bromine was added dropwise to the resulting suspension at 30° C. over a period of 1 hour. The suspension was subjected to reaction at the same temperature for a further 30 minutes, and 43 ml of 1,4-dioxane and 22 ml of water were thereafter added to the reaction mixture with ice-cooling, after which the pH was adjusted to 3.0–4.0 with aqueous ammonia. Then, 7.6 g of thiourea was added to the mixture, and the mixture was subjected to reaction at 30° C. for 2 hours while maintaining the pH in a range of 3.0–5.0 with aqueous ammonia. The reaction mixture was then cooled to 5° C., and the pH was adjusted to 6.5 with aqueous ammonia. The crystals thus obtained were collected by filtration and washed with a mixed solvent of water-1,4-dioxane (1:1) to obtain 18.5 g (yield, 64.2%) of the 1,4-dioxane adduct of 2-(2-aminothiazol-4-yl)-2-(syn)-methoxyiminoacetamide having a melting point of 196°–198° C.

IR(KBr) cm$^{-1}$: $\nu_{C=O}$ 1690

NMR (d$_6$-DMSO) δ value: 3.55 (dioxane), 3.83 (3H, s, —OCH₃), 6.70 (1H, s, thiazole-H), 7.16 (2H, bs, —NH₂), 7.48, 7.77 (1H, bs, —CONH₂), (1H, bs, —CONH₂).

(2) 14.4 g of the 1,4-dioxane adduct of 2-(2-aminothiazol-4-yl)-2-(syn)-methoxyiminoacetamide obtained in above (1) was recrystallized from a mixed solvent of 18 ml of water and 18 ml of methanol to obtain 8.6 g (yield, 86.0%) of 2-(2-aminothiazol-4-yl)-2-(syn)-methoxyiminoacetamide having a melting point of 208°-209° C.

The physical properties (IR, NMR) of the product were identical with those of the product obtained in Example 1-(4).

(3) 1 g of the 1,4-dioxane adduct of 2-(2-aminothiazol-4-yl)-2-(syn)-methoxyiminoacetamide obtained in above (1) was suspended in 5 ml of methanol at 40° C., and the resulting suspension was stirred at the same temperature for 1 hour. The suspension was cooled to room temperature, and the crystals thus obtained were collected by filtration to obtain 2-(2-aminothiazol-4-yl)-2-(syn)-methoxyiminoacetamide having a melting point of 223.5°-225° C. (yield, 89.2%).

The physical property (NMR) of the product was identical with that of the product obtained in Example 1-(4).

EXAMPLE 3

(1) To a mixed solvent of 60 ml of sulfolane and 60 ml of anhydrous methylene chloride which contained 30.6 g of boron trifluoride was added 30.0 g of 2-(2-aminothiazol-4-yl)-2-(syn)-methoxyiminoacetamide. The mixture was subjected to reaction at room temperature for 1 hour, and the crystals thus formed were collected by filtration. The crystals were then suspended in 300 ml of ethyl acetate, and collected by filtration after the resulting suspension had been stirred for 1 hour. They were washed with two 60-ml portions of ethyl acetate and dried to obtain 42.3 g of crystals.

IR(KBr) cm$^{-1}$: 1680, 1650, 1620, 1200–1000

(2) In 41 ml of ethyl acetate was dissolved 4.10 g of pivaloyloxymethyl 7-amino-3-(5-methyl-1,2,3,4-tetrazol-2-yl)methyl-$\Delta^3$-cephem-4-carboxylate, and 3.36 g of the crystals obtained in above (1) were added to the solution, after which the solution was subjected to reaction at room temperature for 3 hours. Then, 41 ml of water was added to the reaction mixture, and the pH was adjusted to 4.5 with sodium hydrogencarbonate. The organic layer was separated, washed with 20 ml of water and dried over anhydrous magnesium sulfate. Then, 2.4 g of mesitylenesulfonic acid dihydrate was added to the organic layer, and the resulting mixture was subjected to reaction at room temperature for 1 hour. The crystals thus formed were collected by filtration and washed with 5 ml of ethyl acetate to obtain 7.18 g (yield, 90.5%) of the mesitylenesulfonic acid salt of pivaloyloxymethyl 7-[2-(2-aminothiazol-4-yl)-2-(syn)-methoxyiminoacetamido]-3-(5-methyl-1,2,3,4-tetrazol-2-yl)methyl-$\Delta^3$-cephem-4-carboxylate having a melting point of 218°-220° C. (decomp).

IR(KBr) cm$^{-1}$: $\nu_{C=O}$ 1782, 1745, 1680

EXAMPLE 4

(1) In 88.8 ml of acetone was suspended 29.6 g of 7-amino-3-(5-methyl-1,2,3,4-tetrazol-2-yl)methyl-$\Delta^3$-cephem-4-carboxylic acid, and 15.2 g of 1,8-diazabicyclo-[5,4,0]-7-undecene was then added dropwise to the resulting suspension at 5° C. After the resulting mixture was subjected to reaction at 5° C. to 10° C. for 30 minutes, the reaction mixture was cooled to 0° C., and 24.2 g of pivaloyloxymethyl iodide was added thereto, after which the mixture was subjected to reaction at 15° C. to 17° C. for 20 minutes. After 385 ml of ethyl acetate had been added dropwise to the reaction mixture over a period of about 5 minutes, 2.37 g of pyridine was added to the mixture and the resulting mixture was stirred for 5 minutes. After the insolubles thus formed had been removed by filtration, the filtrate was cooled to −5° C. To the cooled filtrate was added 33.6 g of the crystals obtained in Example 3-(1), and the resulting mixture was subjected to reaction at −5° C. to 0° C. for 1 hour.

(2) The reaction mixture obtained above (1) was introduced into the solution which had been prepared by adding 19.6 g of 85% by weight phosphoric acid to 207 ml of water and adjusting the pH to 6.5 with 30% aqueous sodium hydroxide solution. The resulting mixture was subjected to reaction at 25° C. to 27° C. for 3 hours while maintaining the pH in a range of 6.2–6.5 with 20% aqueous potassium carbonate solution. Subsequently, the pH was adjusted to 3.0 with hydrochloric acid, and the insolubles were removed by filtration, whereafter the organic layer was separated and washed with 148 ml of water. To the organic layer obtained was added 21.3 g of mesitylenesulfonic acid dihydrate, and the mixture was stirred at 20° C. to 22° C. for 1 hour. The thus precipitated crystals were collected by filtration, washed with three 44-ml portions of ethyl acetate and then dried to obtain 61.9 g (yield, 78.0%) of the mesitylenesulfonic acid salt of pivaloyloxymethyl 7-[2-(2-aminothiazol-4-yl)-2-(syn)-methoxyiminoacetamido]-3-(5-methyl-1,2,3,4-tetrazol-2-yl)methyl-$\Delta^3$-cephem-4-carboxylate having a melting point of 218°-220° C. (decomp.).

IR(KBr) cm$^{-1}$: $\nu_{C=O}$ 1782, 1745, 1680

EXAMPLE 5

The reaction mixture obtained in the same manner as in Example 4-(1) was introduced into the solution which had been prepared by adding 19.6 g of 85% by weight phosphoric acid and 88.8 g of sodium chloride to 266 ml of water and adjusting the pH to 5.3 with 30% aqueous sodium hydroxide solution. The resulting mixture was subjected to reaction at 25° C. to 27° C. for 3 hours while maintaining the pH in a range of 4.8–5.0 with 20% aqueous potassium carbonate solution. Subsequently, the pH was adjusted to 3.0 with hydrochloric acid, and the insolubles were removed by filtration, whereafter the organic layer was separated and washed with 148 ml of water. To the organic layer obtained was added 21.3 g of mesitylenesulfonic acid dihydrate, and the mixture was stirred at 20° C. to 22° C. for 1 hour. The thus precipitated crystals were collected by filtration, washed with three 44-ml portions of ethyl acetate and then dried to obtain 61.9 g (yield, 78.0%) of the mesitylenesulfonic acid salt of pivaloyloxymethyl 7-[2-(2-aminothiazol-4-yl)-2-(syn)-methoxyiminoacetamido]-3-(5-methyl-1,2,3,4-tetrazol-2-yl)methyl-$\Delta^3$-cephem-4-carboxylate having a melting point of 218°-220° C. (decomp).

IR(KBr) cm$^{-1}$: $\nu_{C=O}$ 1782, 1745, 1680

EXAMPLE 6

(1) To the reaction mixture obtained in the same manner as in Example 4-(1) was added 200 ml of ice-water, and the resulting mixture was stirred with ice-cooling for 3 minutes. The organic layer was separated and dried over anhydrous magnesium sulfate, and the solvent was removed by distillation under reduced pressure. To the residue was added 200 ml of diethyl ether, and the crystals thus formed were collected by filtration and then washed with diethyl ether to obtain 59.5 g of crystals.

The physical properties of the crystals obtained were as follows:

IR(KBr) cm$^{-1}$: $\nu_{C=O}$ 1780, 1750

TLC Rf value: 0.69; Developing solvent: benzene:ethyl acetate:methanol=10:10:3; Plate: Merck TLC plate No. 5715.

(2) Into the solution which had been prepared by adding 19.6 g of 85% by weight phosphoric acid to 207 ml of water and adjusting the pH to 6.5 with 30% aqueous sodium hydroxide solution was introduced the solution formed by dissolving 59.5 g of the crystals obtained in above (1) in 385 ml of ethyl acetate. While the mixture was maintained at a pH of 6.2–6.5 with 20% aqueous potassium carbonate solution, the mixture was subjected to reaction at 25° C. to 27° C. for 2 hours. Then, the pH was adjusted to 3.0 with hydrochloric acid, and the insolubles were removed by filtration, whereafter the organic layer was separated and washed with 148 ml of water. Then, 21.3 g of mesitylenesulfonic acid dihydrate was added to the organic layer obtained, and the mixture was stirred at 20° C. to 22° C. for 1 hour. The thus precipitated crystals were collected by filtration, washed with three 44-ml portions of ethyl acetate and dried to obtain 55.5 g of the mesitylenesulfonic acid salt of pivaloyloxymethyl 7-[2-(2-aminothiazol-4-yl)-2-(syn)-methoxyiminoacetamido]-3-(5-methyl-1,2,3,4-tetrazol-2-yl)methyl-$\Delta^3$-cephem-4-carboxylate having a melting point of 218°–220° C. (decomp.).

IR(KBr) cm$^{-1}$: $\nu_{C=O}$ 1782, 1745, 1680

EXAMPLE 7

(1) In 13 ml of anhydrous methylene chloride was suspended 6.0 g of 2-(2-aminothiazol-4-yl)-2-(syn)-methoxyiminoacetamide. To the resulting suspension was added 10.3 ml of a mixed solution of sulfolane and anhydrous methylene chloride (1:1 by volume) containing 2.72 g of boron trifluoride at 15° C. to 20° C., and the resulting mixture was subjected to reaction at the same temperature for 10 minutes. Then, to the mixture was added 13 ml of anhydrous methylene chloride containing 4.10 g of pivaloyloxymethyl 7-amino-3-(5-methyl-1,2,3,4-tetrazol-2-yl)methyl-$\Delta^3$-cephem-4-carboxylate, and the resulting mixture was subjected to reaction at 30° C. to 35° C. for 2.5 hours. The reaction mixture was then introduced into 15 ml of ice-water, and the pH was adjusted to 5.5 with saturated aqueous sodium hydrogencarbonate solution. After the insolubles had been removed, the organic layer was separated, washed with 15 ml of saturated aqueous sodium chloride solution, and then dried over anhydrous magnesium sulfate. The solvent was removed by distillation under reduced pressure, and 60 ml of ethyl acetate was added to the residue thus obtained to form a solution, to which 2.36 g of mesitylenesulfonic acid dihydrate was then added. The resulting mixture was stirred for 30 minutes, and the resulting precipitates were collected by filtration to obtain 6.37 g (yield, 80.2%) of the mesitylenesulfonic acid salt of pivaloyloxymethyl 7-[2-(2-aminothiazol-4-yl)-2-(syn)-methoxyiminoacetamido]-3-(5-methyl-1,2,3,4-tetrazol-2-yl)methyl-$\Delta^3$-cephem-4-carboxylate having a melting point of 218°–220° C. (decomp.).

IR(KBr) cm$^{-1}$: $\nu_{C=O}$ 1782, 1745, 1680

(2) When the same procedure as in above (1) was repeated, except that the reaction conditions shown in Table 2 were used, the mesitylenesulfonic acid salt of pivaloyloxymethyl 7-[2-(2-aminothiazol-4-yl)-2-(syn)-methoxyiminoacetamido]-3-(5-methyl-1,2,3,4-tetrazol-2-yl)methyl-$\Delta^3$-cephem-4-carboxylate was obtained.

The physical properties (melting point, IR) of the product were identical with those of the product obtained in above (1).

TABLE 2

| No. | 2-(2-Aminothiazol-4-yl)-2-(syn)-methoxyiminoacetamide (g) | Pivaloyloxymethyl 7-amino-3-(5-methyl-1,2,3,4-tetrazol-2-yl)-methyl-$\Delta^3$-cephem-4-carboxylate (g) | BF$_3$ (g)/Solvent* | Reaction solvent | Reaction temperature (°C.) Reaction time (hour) | Amount of product (g)/ Yield (%) |
|---|---|---|---|---|---|---|
| 1 | 4.0 | 4.1 | 2.04/Sulfolane | Methylene chloride | 30 8 | 5.94/74.8 |
| 2 | 6.0 | 4.1 | 2.72/Acetonitrile | Acetonitrile | 50 5 | 6.3/79.4 |
| 3 | 6.0 | 4.1 | 2.72/Sulfolane + Methylene chloride | Nitromethane | 30 3 | 6.4/80.6 |
| 4 | 6.0 | 4.1 | 2.72/Ethyl acetate | Methylene chloride + Ethyl acetate | 30 3 | 6.4/80.6 |

Note: *This solvent refers to a solvent in which BF$_3$ is dissolved or which forms a complex compound with BF$_3$.

(3) When the same procedure as in above (1) was repeated, except that the starting compounds shown in Table 3 were used in place of the 2-(2-aminothiazol-4-yl)-2-(syn)-methoxyiminoacetamide, the mesitylenesulfonic acid salt of pivaloyloxymethyl 7-[2-(2-aminothiazol-4-yl)-2-(syn)-methoxyiminoacetamido]-3-(5-methyl-1,2,3,4-tetrazol-2-yl)methyl-$\Delta^3$-cephem-4-carboxylate was obtained.

The physical properties (melting point, IR) of the product were identical with those of the product obtained in above (1).

TABLE 3

| No. | Starting Compound | Yield (%) |
|---|---|---|
| 1 | N—ethyl-2-(2-aminothiazol-4-yl)-2-(syn)-methoxyiminoacetamide | 75.0 |
| 2 | N—phenyl-2-(2-aminothiazol-4-yl)-2-(syn)-methoxyiminoacetamide | 80.2 |
| 3 | N—p-nitrophenyl-2-(2-aminothiazol-4-yl)-2-(syn)-methoxyiminoacetamide | 82.0 |
| 4 | N—(pyridin-4-yl)-2-(2-aminothiazol-4-yl)-2-(syn)-methoxyiminoacetamide | 65.8 |

EXAMPLE 8

(1) In 13 ml of anhydrous methylene chloride was suspended 6.0 g of 2-(2-aminothiazol-4-yl)-2-(syn)-methoxyiminoacetamide. To the resulting suspension was added 10.3 ml of a mixed solution of sulfolane and anhyrdrous methylene chloride (1:1 by volume) containing 2.72 g of boron trifluoride at 15° C. to 20° C., and the mixture was subjected to reaction at the same temperature for 10 minutes. To the mixture was then added 40 ml of anhydrous methylene chloride containing 4.62 g of diphenylmethyl 7-amino-3-(5-methyl-1,2,3,4-tetrazol-2-yl)methyl-Δ³-cephem-4-carboxylate, and the resulting mixture was subjected to reaction at 30° C. to 35° C. for 3 hours. The reaction mixture was introduced into 50 ml of water, and the pH was adjusted to 5.5 with sodium hydrogencarbonate. After the insolubles had been removed, the organic layer was separated, washed with 20 ml of saturated aqueous sodium chloride solution, and dried over anhydrous magnesium sulfate. The solvent was removed by distillation under reduced pressure, and the residue obtained was purified by a column chromatography (Wako Silica Gel C-200, eluant: chloroform-methanol) to obtain 4.2 g (yield, 65.1%) of diphenylmethyl 7-[2-(2-aminothiazol-4-yl)-2-(syn)-methoxyiminoacetamido]-3-(5-methyl-1,2,3,4-tetrazol-2-yl)methyl-Δ³-cephem-4-carboxylate having a melting point of 102°–105° C. (decomp.).

IR(KBr) cm⁻¹: $\nu_{C=O}$ 1778, 1720, 1660

The compounds shown in Table 4 were obtained in a similar manner.

TABLE 4

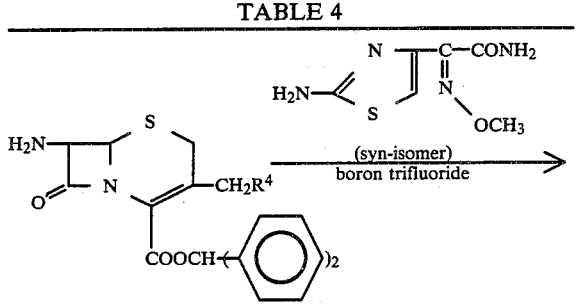

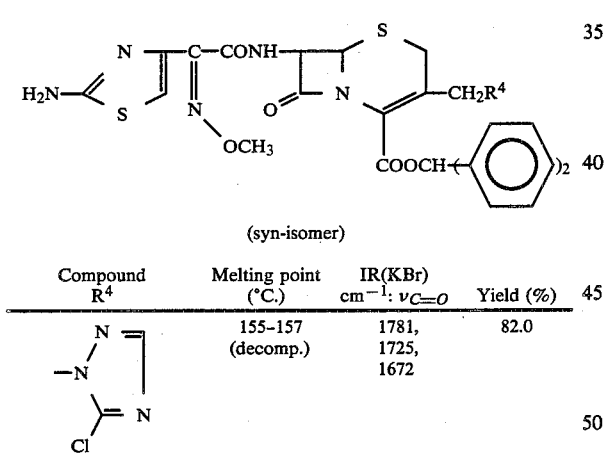

(syn-isomer)

| Compound R⁴ | Melting point (°C.) | IR(KBr) cm⁻¹: $\nu_{C=O}$ | Yield (%) |
|---|---|---|---|
| 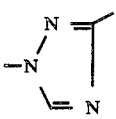 | 155–157 (decomp.) | 1781, 1725, 1672 | 82.0 |

TABLE 4-continued

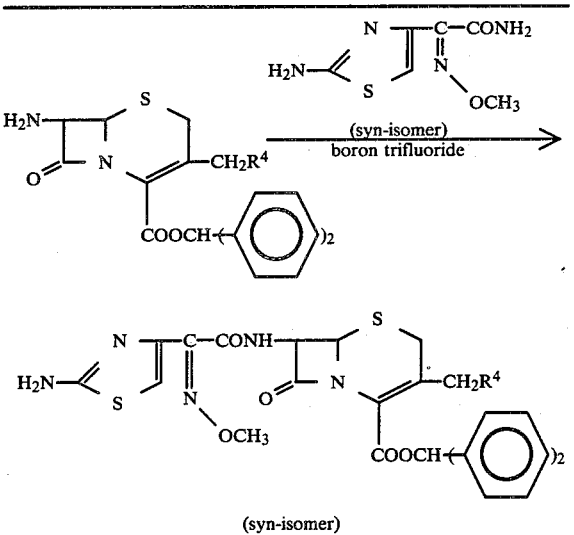

(syn-isomer)

| Compound R⁴ | Melting point (°C.) | IR(KBr) cm⁻¹: $\nu_{C=O}$ | Yield (%) |
|---|---|---|---|
| 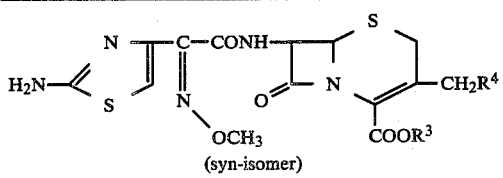 | 166–167 (decomp.) | 1780, 1720, 1680, 1650 | 80.0 |

(2) In a mixed solvent of 35 ml of trifluoroacetic acid and 10 ml of anisole was dissolved 6.45 g of diphenylmethyl 7-[2-(2-aminothiazol4-yl)-2-(syn)-methoxyiminoacetamido]-3-(5-methyl-1,2,3,4-tetrazol-2-yl)methyl-Δ³-cephem-4-carboxylate, and the resulting mixture was subjected to reaction at room temperature for 1 hour. The solvent was removed by distillation under reduced pressure, and diethyl ether was added to the residue thus obtained. The resulting crystals were collected by filtration, washed well with diethyl ether, and then dried to obtain 5.46 g (yield, 92.1%) of the trifluoroacetic acid salt of 7-[2-(2-aminothiazol-4-yl)-2-(syn)-methoxyiminoacetamido]-3-(5-methyl-1,2,3,4-tetrazol-2-yl)-methyl-Δ³-cephem-4-carboxylic acid having a melting point of 123°–125° C. (decomp.).

IR(KBr) cm⁻¹: $\nu_{C=O}$ 1790, 1720–1635

EXAMPLE 9

The compounds shown in Table 5 were obtained in a yield of 65–85% in a similar manner to that in Example 2, 3, 4, 5, 6, 7 or 8.

TABLE 5

(syn-isomer)

| Compound | | Melting point (°C.) | IR(KBr) cm⁻¹: $\nu_{C=O}$ |
|---|---|---|---|
| R³ | R⁴ | | |
| —CH₂OCOC(CH₃)₃* | (N-methyltetrazol-CH₃) | 144–146 (decomp.) | 1780, 1745, 1660 |

TABLE 5-continued

Structure (syn-isomer): aminothiazolyl-methoxyimino-cephem with -COOR³ and -CH₂R⁴ substituents.

| R³ | R⁴ | Melting point (°C.) | IR(KBr) cm⁻¹: ν$_{C=O}$ |
|---|---|---|---|
| —CH₂OCOC(CH₃)₃* | 4-methylthio-1,2,4-triazol-1-yl (SCH₃ substituted triazole, N-linked) | 135–137 (decomp.) | 1785, 1745, 1672 |
| —CH₂OCOC(CH₃)₃ | 5-methyl-1,2,3-triazol-1-yl (CH₃ substituted, N=N containing) | 127–128 (decomp.) | 1780, 1743, 1675 |
| —CH₂OCOC(CH₃)₃ | 1,2,4-triazol-1-yl | 130–132 (decomp.) | 1780, 1745, 1665 |
| —CH₂OCOC(CH₃)₃ | 3-chloro-1,2,4-triazol-1-yl | 118–122 (decomp.) | 1780, 1745, 1670 |
| —CH₂OCOC(CH₃)₃ | 3-ethyl-2,4-dioxo-3,4-dihydropyrimidin-1-yl (N—CH₂CH₃) | 145–147 | 1780, 1740, 1675, 1640 |
| —CH₂OCOC(CH₃)₃ | 2-oxopyrazin-1-yl | 134–137 (decomp.) | 1780, 1750, 1680–1650 |
| —CH₂OCOC(CH₃)₃ | 6-methyl-3-oxopyridazin-2-yl (CH₃) | 141–142 (decomp.) | 1775, 1740, 1650 |
| —CH₂OCOC(CH₃)₃ | 5,6-dimethyl-3-oxopyrazin-1-yl (CH₃, CH₃) | 156–159 | 1775, 1740, 1670–1640 |
| —CH₂OCOC(CH₃)₃ | 3,6-dioxo-1,2,3,6-tetrahydropyridazin-1-yl (HN, N linked, with two C=O) | 151–153 (decomp.) | 1780, 1745, 1660 |

TABLE 5-continued

Structure: (syn-isomer)

$H_2N$-thiazole-C(=NOCH$_3$)-CONH-[β-lactam]-CH$_2$R$^4$, COOR$^3$

| R$^3$ | R$^4$ | Melting point (°C.) | IR(KBr) cm$^{-1}$: $\nu_{C=O}$ |
|---|---|---|---|
| —CH$_2$OCOC(CH$_3$)$_3$ | 4-methyl-6-oxo-pyrimidin-1-yl | 124–125 (decomp.) | 1780, 1745, 1680, 1670 |
| —CH$_2$OCOC(CH$_3$)$_3$ | 6-oxo-pyrimidin-1-yl | 160–164 (decomp.) | 1785, 1750, 1665 |
| —CH$_2$OCOC(CH$_3$)$_3$ | 4,6-dimethyl-2-oxo-pyrimidin-1-yl | 139–141 (decomp.) | 1780, 1740, 1690–1660 |
| —CH$_2$OCOC(CH$_3$)$_3$ | 4,6-dimethyl-1,1-dioxo-1,2,6-thiadiazin-2-yl | 116–118 (decomp.) | 1780, 1745, 1670 |
| —CH$_2$OCOC(CH$_3$)$_3$ | 3-methyl-1,1-dioxo-thiadiazinane-2-yl | 112–113 | 1780, 1750, 1675 |
| —CH$_3$* | 3-methyl-1,2,4-triazol (N=N, CH$_3$) | 154 (decomp.) | 1785, 1730, 1655 |
| —(CH$_2$)$_3$CH$_3$ | 3-ethyl-2,4-dioxo-pyrimidin-1-yl | 139–144 (decomp.) | 1780, 1720, 1680, 1640 |
| —CHOCOC(CH$_3$)$_3$ \| CH$_3$ | 3-methyl-1,2,4-triazol | 127–130 (decomp.) | 1780, 1740, 1675 |

TABLE 5-continued

[Structure: syn-isomer of cephalosporin with H₂N-thiazole, C-CONH, N-OCH₃, S, CH₂R⁴, COOR³]

| Compound | | Melting point (°C.) | IR(KBr) cm⁻¹: $\nu_{C=O}$ |
|---|---|---|---|
| R³ | R⁴ | | |
| —CHOCOC(CH₃)₃<br>\|<br>CH₃ | [N-N triazole with Cl, =N] | 145–147 | 1780, 1745, 1670 |
| —CHOCOC(CH₃)₃<br>\|<br>CH₃ | [pyrimidinedione with N—CH₃] | 198–201 (decomp.) | 1780, 1740, 1680–1640 |
| —CHOCOC(CH₃)₃<br>\|<br>CH₃ | [pyrimidinedione with N—CH₂CH₃] | 148–150 | 1780, 1740, 1680, 1640 |
| —CHOCOC(CH₃)₃<br>\|<br>CH₃ | [pyrimidinedione with N—(CH₂)₄CH₃] | 139–141 (decomp.) | 1783, 1740, 1680, 1640 |
| —CHOCOC(CH₃)₃<br>\|<br>CH₃ | [pyrimidinedione with N—(CH₂)₅CH₃] | 145–150 (decomp.) | 1780, 1740, 1685, 1645 |
| —CHOCOC(CH₃)₃<br>\|<br>CH₃ | [pyrimidinedione with N—(CH₂)₇CH₃] | 170–172 (decomp.) | 1780, 1740, 1680, 1640 |
| —CHOCOC(CH₃)₃<br>\|<br>CH₃ | [pyrimidinedione with N—(CH₂)₁₁CH₃] | 153–158 (decomp.) | 1780, 1745, 1675, 1640 |
| —CHOCOC(CH₃)₃<br>\|<br>CH₃ | [pyridazinone with CH₃] | 143–145 (decomp.) | 1780, 1740, 1655 |
| —CHOCOC(CH₃)₃<br>\|<br>CH₃ | [pyrimidinone with CH₃] | 112–116 (decomp.) | 1780, 1740, 1660 |

TABLE 5-continued

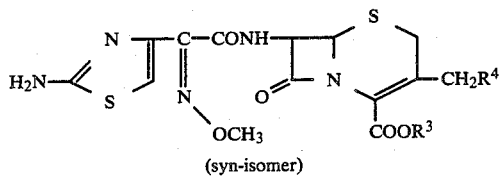
(syn-isomer)

| R³ | R⁴ | Melting point (°C.) | IR(KBr) cm⁻¹: $\nu_{C=O}$ |
|---|---|---|---|
| —CHOCOC(CH₃)₃<br>\|<br>CH₃ | (N-methyl-dimethyl-oxo-pyrimidinyl group with CH₃, CH₃, C=O) | 118–121 (decomp.) | 1780, 1740, 1660 |
| —CHOCOC(CH₃)₃*<br>\|<br>CH₃ | 1-methyl-tetrazolyl (—N—N=N, N=N, CH₃) | 150–160 (decomp.) | 1793, 1742, 1675 |
| (phthalidyl)* | 1-methyl-tetrazolyl | 166–168 (decomp.) | 1775, 1745, 1665 |
| (phthalidyl)*<br>** | (N-ethyl-dioxo-pyrimidinyl, —N—CH₂CH₃) | >200 | 1780, 1680, 1640 |
| —CH₂OCOCH₃ | 1-methyl-tetrazolyl | 121–124 (decomp.) | 1780, 1745, 1670 |
| —CH₂OCO(CH₂)₃CH₃ | 1-methyl-tetrazolyl | 107–108 | 1780, 1760, 1670 |
| —CHOCOC(CH₃)₃<br>\|<br>CH₂<br>\|<br>CH₃ | 1-methyl-tetrazolyl | 140–142 (decomp.) | 1785, 1745, 1675 |
| —CHOCOC(CH₃)₃<br>\|<br>(phenyl) | 1-methyl-tetrazolyl | 153–157 (decomp.) | 1785, 1745, 1680 |

TABLE 5-continued
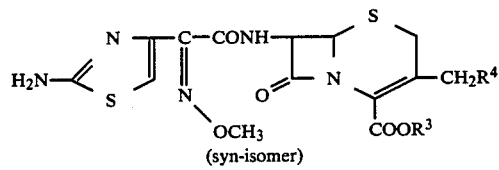
(syn-isomer)
| Compound | | | |
|---|---|---|---|
| R³ | R⁴ | Melting point (°C.) | IR(KBr) cm⁻¹: ν$_{C=O}$ |
| -CHOCO-⬡-<br>  \|<br>  CH₃ | -N(N=N)N=C-CH₃ (triazole) | 125 (decomp.) | 1780, 1740, 1675 |
Note:
*Hydrochloride (Hydrochlorides were obtained in a conventional manner.)
**Diastereomer
What is claimed is:
1. A compound represented by the formula [II]:
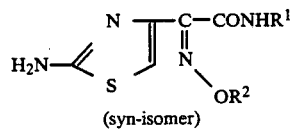
(syn-isomer)
wherein $R^1$ is a hydrogen atom and $R^2$ is a lower alkyl group.
* * * * *